United States Patent

Pelosi, Jr. et al.

[11] 4,217,286
[45] Aug. 12, 1980

[54] 5-PHENYL-2-FURANCARBOXIMIDAMIDES

[75] Inventors: Stanford S. Pelosi, Jr.; Ronald E. White; George C. Wright; Chia N. Yu, all of Norwich, N.Y.

[73] Assignee: Morton-Norwich Products, Inc., Norwich, N.Y.

[21] Appl. No.: 765,623

[22] Filed: Jan. 25, 1977

[51] Int. Cl.² ............................................. C07D 307/68
[52] U.S. Cl. .................................... 260/347.7; 427/285
[58] Field of Search ........................................ 260/347.7

[56] References Cited
U.S. PATENT DOCUMENTS 3,906,010   9/1975   Pelosi et al. ................... 260/347.7 X Primary Examiner—Richard Raymond
Attorney, Agent, or Firm—Anthony J. Franze

[57] ABSTRACT

Certain 5-phenyl-2-furancarboximidamides of the formula:

wherein X represents 2-nitro, 2-amino or 4-amino; $R_1$ represents hydrogen or butyl; $R_2$ represents butyl, hexyl or 3,4-dichlorobenzyl are effective antibacterial agents.

2 Claims, No Drawings

5-PHENYL-2-FURANCARBOXIMIDAMIDES

This invention relates to chemical compounds. More particularly, this invention relates to certain 5-phenyl-2-furancarboximidamides of the formula:

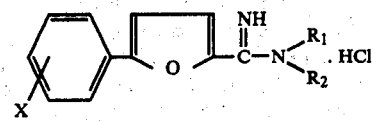

wherein X represents 2-nitro, 2-amino or 4-amino; $R_1$ represents hydrogen or butyl; $R_2$ represents butyl, hexyl or 3,4-dichlorobenzyl and a method for their preparation. The compounds of this invention possess antibacterial activity. They are particularly inimical to *Staphylococcus aureus* in the commonly employed in vitro technique for determining antibacterial activity at levels of from 3.1 to 31. mcg of compound per milliliter of test media. They are thus adapted to be combined in various forms such as ointments, powders, solutions, sprays, dusts and the like in a concentration of from 0.1 to 1% by weight suitable for application to prevent bacterial contamination.

The compounds of this invention are readily prepared. Currently, it is preferred to prepare these compounds according to the following scheme:

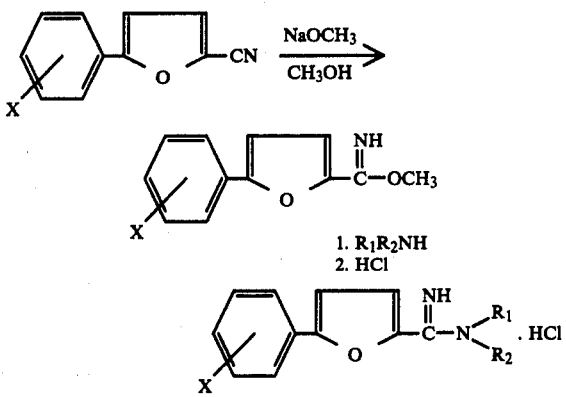

In the above scheme, X, $R_1$, and $R_2$ have the significance previously ascribed.

In order that this invention may be fully available to and understood by those skilled in the art, the following examples are supplied.

EXAMPLE I

N-(3,4-Dichlorobenzyl)-5-(2-nitrophenyl)-2-furancarboximidamide Hydrochloride

A mixture of 5-(2-nitrophenyl)-2-furonitrile (92 g, 0.43 mole) and anhydrous methanol (1000 ml) was heated to 55° and sodium methoxide (1.5 g) was added. The steam bath was removed, the solution was stirred for two hours and stored overnight at room temperature. The solution was poured into ice water (1000 ml) and stirred for one hour. The product was collected by filtration and air dried to yield 91 g (86%) of methyl 5-(2-nitrophenyl)-2-furancarboximidate. A sample was recrystallized from isopropanol, m.p. 107°–108°.

Anal. Calcd. for $C_{12}H_{10}N_2O_4$: C, 58.54; H, 4.09; N, 11.38. Found: C, 58.56; H, 3.87; N, 11.26.

A mixture of the above compound (50 g, 0.20 mole), ethanol (500 ml), and 3,4-dichlorobenzylamine (35.2 g, 0.20 mole) was stirred at room temperature for 16 hours and then refluxed for 8 hours. The mixture was filtered, the filtrate stripped of solvent under reduced pressure, and the residue was washed with cyclohexane. The cyclohexane was decanted, and the residue was dissolved in ether, stirred over Darco, and filtered. The filtrate was adjusted to pH 2 with ether/HCl and the product was collected by filtration, yield: 45 g (53%). A sample was recrystallized from methanol, m.p. 274°–278°.

Anal. Calcd. for $C_{18}H_{13}Cl_2N_3O_3 \cdot HCl$: C, 50.67; H, 3.31; N, 9.85. Found: C, 50.48; H, 3.35; N, 9.86.

EXAMPLE II 5-(2-Aminophenyl)-N-(3,4-dichlorobenzyl)-2-furancarboximidamide Hydrochloride Methanolate The mixture of the compound of Example I (31 g, 0.073 mole), ethanol (350 ml) and 5% Pd/C-50% $H_2O$ (1.5 g) was subjected to hydrogenation for 5 hours at room temperature, using 14.0 psia $H_2$ (theory: 14.7 psia). Methanol (1000 ml) was added to the reaction mixture. The mixture was heated, treated with Darco, filtered, and the filtrate was reduced in volume to 400 ml under reduced pressure. The mixture was cooled and the product was collected by filtration. The product was recrystallized from methanol: m.p. 225°–257°, yield: 10 g (34%).

Anal. Calcd. for $C_{18}H_{15}Cl_2N_3O \cdot HCl \cdot \frac{1}{4}CH_3OH$: C, 54.16; H, 4.23; N, 10.38. Found C, 53.96; H, 4.23; N, 10.43.

EXAMPLE III

N-Hexyl-5-(2-nitrophenyl)-2-furancarboximidamide Hydrochloride

A mixture of methyl 5-(2-nitrophenyl)-2-furancarboximidate (50 g, 0.2 mole), ethanol (500 ml), and n-hexylamine (20.2 g, 0.2 mole) was stirred 16 hours at room temperature and then refluxed for 8 hours. The mixture was stripped of solvent under reduced pressure, and the residue was washed with hot cyclohexane. The residue was dissolved in anhydrous ether, the solution was adjusted to pH 2 with ether/HCl, and the product was collected by filtration. The product was recrystallized from acetonitrile; m.p. 173°–175°, yield: 20 g (41%).

Anal. Calcd. for $C_{17}H_{21}N_3O_3 \cdot HCl$: C, 58.03; H, 6.30; N, 11.95. Found: C, 58.03; H, 6.31; N, 11.88.

EXAMPLE IV 5-(2-Aminophenyl)-N-hexyl-2-furancarboximidamide Hydrochloride

A mixture of the compound of Example III (17 g, 0.048 mole), ethanol (250 ml), and 5% Pd/C-50% $H_2O$ (1.0 g) was subjected to hydrogenation at room temperature for 4 hours, using 6.0 psia $H_2$ (theory: 5.9 psia $H_2$). The catalyst was removed by filtration, the filtrate was diluted with anhydrous ether (1000 ml), and cooled. The product was collected by filtration and air dried; m.p. 148°–150°, yield: 15 g (97%).

Anal. Calcd. for $C_{17}H_{23}N_3O \cdot HCl$: C, 63.44; H, 7.52; N, 13.06. Found: C, 63.17; H, 7.47; N, 13.01.

EXAMPLE V

5-(4-Aminophenyl)-N,N-dibutyl-2-furancarboximidamide Tetartohydrate

A mixture of 10.7 (0.05 ml) of 5-(4-nitrophenyl)-2-furonitrile and 500 ml of anhydrous methanol was heated on a steam bath until a solution resulted. After slight cooling, a catalytic amount (0.1 g) of powdered sodium methoxide was added with stirring. The solution turned quite dark and in about 5 minutes, solid started to separate. The mixture was allowed to stir for an hour and then was filtered. The solid was washed with anhydrous methanol and air dried. The yield was 10.0 g (81%). Recrystallization from 200 ml of ethyl acetate gave 6.0 g of analytically pure methyl 5-(4-nitrophenyl)-2-furancarboximidate, m.p. 184°–188°.

Anal. Calcd. for $C_{12}H_{10}N_2O_4$: C, 58.54; H, 4.09; N, 11.38. Found: C, 58.19; H, 4.06; N, 11.26.

A mixture of the above compound (36 g, 0.15 mole), ethanol (500 ml) and dibutylamine (39 g, 0.30 mole) was refluxed for 22 hours and cooled to room temperature. The mixture was concentrated under reduced pressure to 150 ml and the mixture was filtered. The filtrate was stripped of solvent under reduced pressure and the residue was washed with water. The residue was dissolved in ether, dried over $MgSO_4$ and Darco, filtered, and the filtrate was stripped of solvent under reduced pressure. The residue was dissolved in isopropanol, and the solution was adjusted to pH 2 with ether/HCl and cooled. The solid was collected by filtration to yield 13 g (23%) of N,N-dibutyl-5-(4-nitrophenyl)-2-furancarboximidamide, m.p. 196°–200°.

A mixture of N,N-dibutyl-5-(4-nitrophenyl)-2-furancarboximidamide hydrochloride (12 g, 0.032 mole), ethanol (100 ml) and 5% Pd/C-50% $H_2O$ (0.5 g) was subjected to hydrogenation at room temperature for 8½ hours, using 10 psia $H_2$ (theory, 8.2 psia $H_2$). The catalyst was removed by filtration, the filtrate was diluted with anhydrous ether (300 ml), and the mixture was cooled. The solid material was collected by filtration, added to $H_2O$ (1000 ml), and the solution was adjusted to pH 10 with 20% aqueous NaCH. The product was collected by filtration and recrystallized from cyclohexane, yield: 3.5 g (34%). A sample was recrystallized from cyclohexane, m.p. 100°–101°

Anal. Calcd. for $C_{19}H_{27}N_3O.\frac{1}{4}CH_2O$: C, 71.77; H, 8.72; N, 13.22; $H_2O$, 1.42. Found: C, 71.86; H, 8.60; N, 13.09; $H_2O$, 0.7.

What is claimed is:

1. The compound N-(3,4-dichlorobenzyl)-5-(2-nitrophenyl)-2-furancarboximidamide hydrochloride.
2. The compound 5-(2-aminophenyl)-N-(3,4-dichlorobenzyl)-2-furancarboximidamide hydrochloride methanolate.

* * * * *